(12) United States Patent
Makino et al.

(10) Patent No.: US 9,080,972 B2
(45) Date of Patent: Jul. 14, 2015

(54) AUTOMATIC ANALYZER

(75) Inventors: Akihisa Makino, Hitachinaka (JP);
Sakuichiro Adachi, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 47 days.

(21) Appl. No.: 13/979,668

(22) PCT Filed: Jan. 10, 2012

(86) PCT No.: PCT/JP2012/050243
§ 371 (c)(1),
(2), (4) Date: Jul. 15, 2013

(87) PCT Pub. No.: WO2012/098946
PCT Pub. Date: Jul. 26, 2012

(65) Prior Publication Data
US 2013/0301048 A1 Nov. 14, 2013

(30) Foreign Application Priority Data
Jan. 17, 2011 (JP) .................................. 2011-006809

(51) Int. Cl.
G01N 21/53 (2006.01)
G01N 21/49 (2006.01)
G01N 21/51 (2006.01)
G01N 35/00 (2006.01)

(52) U.S. Cl.
CPC ................ G01N 21/49 (2013.01); G01N 21/51 (2013.01); G01N 35/00693 (2013.01); *G01N 2201/0415* (2013.01); *G01N 2201/1211* (2013.01)

(58) Field of Classification Search
USPC .................. 356/335–344, 445–448, 450–458
See application file for complete search history.

(56) References Cited

U.S. PATENT DOCUMENTS

| 4,373,818 | A | * | 2/1983 | Yamamoto et al. | ........... 356/408 |
| 4,408,880 | A | * | 10/1983 | Tsuji et al. | ..................... 356/338 |
| 4,420,256 | A | * | 12/1983 | Fladda et al. | ................ 356/336 |
| 4,451,433 | A | | 5/1984 | Yamashita et al. | |
| 4,690,562 | A | | 9/1987 | Davies et al. | |

(Continued)

FOREIGN PATENT DOCUMENTS

| JP | 61-82143 A | 4/1986 |
| JP | 05-045282 A | 2/1993 |
| JP | 2002-296283 A | 10/2002 |
| JP | 2007-322246 A | 12/2007 |
| WO | 2010/073604 A1 | 7/2010 |
| WO | 2011/004781 A1 | 1/2011 |

OTHER PUBLICATIONS

English language translation of the Japanese Office Action received in corresponding Japanese Application No. 2011-006809 dated Jul. 23, 2013.

*Primary Examiner* — Kara E Geisel
*Assistant Examiner* — Jarreas C Underwood
(74) *Attorney, Agent, or Firm* — Mattingly & Malur, PC

(57) ABSTRACT

The scattered light from the measurement target substance passes through a light receiving window, and is received by a detector for $+\theta$ scattered light and a detector for $-\theta$ scattered light which are arranged symmetrically to each other across an optical axis at an equal angle or an equal interval in a vertical direction. A light source is fixed by a light-source holder (that is a base member on which the light source is arranged), and the detectors are arranged on and fixed to a detector holder (that is a base member on which the detectors are arranged). In this manner, drift of the light quantity data caused by the thermal deformation of the optical system can be corrected by comparing values of the light quantity data of the detectors.

7 Claims, 6 Drawing Sheets

(56) References Cited

U.S. PATENT DOCUMENTS

| | | | |
|---|---|---|---|
| 4,828,388 A * | 5/1989 | Namba | 356/336 |
| 5,350,922 A * | 9/1994 | Bartz | 250/338.5 |
| 5,499,313 A * | 3/1996 | Kleinerman | 385/123 |
| 6,519,033 B1 * | 2/2003 | Quist et al. | 356/337 |
| 6,574,425 B1 * | 6/2003 | Weiss et al. | 356/402 |
| 7,111,496 B1 * | 9/2006 | Lilienfeld et al. | 73/28.01 |
| 7,990,525 B2 * | 8/2011 | Kanda | 356/73 |
| 2011/0255090 A1 | 10/2011 | Harada et al. | |

* cited by examiner

AUTOMATIC ANALYZER

TECHNICAL FIELD

The present invention relates to an automatic analyzer that analyzes an amount of a component contained in a sample such as blood or urine, and, more particularly, the present invention relates to a technique enabling correction of drift caused by thermal deformation of an optical system.

BACKGROUND ART

As an analyzer that analyzes an amount of a component contained in a sample, an automatic analyzer is widely used, in which the amount of the component is determined from a relation between absorbance and a concentration in accordance with the Lambert-Beer law by irradiating a sample or reaction solution of a mixture of the sample and a reagent with light from a light source, measuring transmitted light quantity at a single or a plurality of wavelength (s) as a result obtained by the irradiation, and calculating an absorbance (see Patent Document 1).

In such a device, many reaction containers retaining the reaction solution are circumferentially arranged on a reaction disk which repeatedly rotates and stops, and time-dependent change of the absorbance is measured at a constant time interval for about minutes during the rotation of the reaction disk by a transmitted-light measuring unit previously arranged. After the measurement is terminated, the reaction containers are cleaned by a cleaning mechanism and are used for the re-analysis.

As the reaction of the reaction solution, roughly two types of reactions including color reaction between a substrate and an enzyme and agglutination reaction between an antigen and an antibody are used.

The former one is biochemical analysis having test items which are LDH (Lactate Dehydrogenase), ALP (Alkaline Phosphatase), AST (Aspartate Aminotransferase), and others. The latter one is immuno-analysis having tested items which are CRP (C-reactive protein), IgG (Immunoglobulin G), RF (Rheumatoid factor), and others.

A blood concentration of a measurement substance measured in the immuno-analysis of the latter one is low, and therefore, a highly sensitive detection system is required. For example, the high sensitivity has been advanced by a latex agglutination method that quantifies the amount of the component contained in the sample by: using a reagent which is obtained by sensitizing (coupling) an antibody onto surfaces of latex particles, irradiating a reaction solution with light upon the agglutination of the latex particles by antigen-antibody reaction with an antigen contained in the sample, and measuring the quantity of the light transmitted without being scattered by latex agglutinate.

Further, as an automatic analyzer, the high sensitivity has been attempted by measuring not the transmitted light quantity but the scattered light quantity.

Incidentally, in achieving the high sensitivity, even drift of light quantity data caused by slight variation in a temperature in the device becomes a large problem when change of minute light quantity is detected at high sensitivity. It is considered that the drifts of the light quantity data are roughly categorized into (1) drift of a light source, (2) drift of an electric circuit system, and (3) drift caused by thermal deformation of an optical system. Regarding (1) the drift of the light source, a technique of monitoring the irradiation light quantity for the correction (see Patent Document 2) is known. Regarding (2) the drift of the electric circuit system, a technique of suppressing the circuit-derived drift by controlling a temperature in a circuit board storage is known (see Patent Document 3).

PRIOR ART DOCUMENTS

Patent Documents

Patent Document 1: U.S. Pat. No. 4,451,433
Patent Document 2: Japanese Patent Application Laid-Open Publication No. 2007-322246
Patent Document 3: Japanese Patent Application Laid-Open Publication No. 2002-296283

DISCLOSURE OF THE INVENTION

Problems to be Solved by the Invention

However, in both of the proposals of Patent Documents 2 and 3, (3) the drift caused by thermal deformation of the optical system is not taken into consideration.

The thermal deformation of the optical system is affected by not only thermal deformation of a photometer but also thermal deformation of a mechanism base on which the photometer is mounted, and these thermal deformations are affected by complex temperature changes between the outside temperature and heat sources (a motor, a board, a heat exchanger, etc.) which are individually operated and controlled, and therefore, control for them is extremely difficult. Further, in a turntable-type automatic analyzer which performs the measurement while rotating the reaction disk, the photometer inevitably has a shape with a cut-out region through which the reaction container passes, and the shape is a disadvantageous shape for the thermal deformations.

Here, for example, it is considered to provide a storage for housing the photometer and adjusting the temperature so as not to be affected by the heat sources, etc. However, by adding new equipment, a size of the device is increased, and the device is complicated adversely.

A preferred aim of the present invention is to provide an automatic analyzer enabling to detect a measurement target substance at high sensitivity without causing the size increase and the complication of the device by correcting the variation in light quantity data caused by the thermal deformation of the optical system caused by the variation in the temperature inside the device.

The above and other preferred aims and novel characteristics of the present invention will be apparent from the description of the present specification and the accompanying drawings.

Means for Solving the Problems

The typical ones of the inventions disclosed in the present application will be briefly described as follows.

An automatic analyzer according to a typical embodiment is an automatic analyzer which includes: a light source which irradiates a reaction container arranged at a photometric position and housing mixture solution of a sample and a reagent with light; and a detector which detects scattered light or transmitted light from the mixture solution, in which at least a pair of the detectors are arranged symmetrically to each other across an optical axis of the irradiation light from the light source in a vertical direction, and in which an averaged value of the light quantity data and/or a sum thereof from the respective detectors is used for calculation of a concentration of a measurement target substance in the mixture solution.

An automatic analyzer according to a typical embodiment is an automatic analyzer which irradiates a reaction container arranged at a photometric position and housing mixture solution of a sample and a reagent with light from a light source, which detects scattered light or transmitted light from the mixture solution by a detector to obtain light quantity data, and which calculates a concentration of a measurement target substance in the mixture solution from the light quantity data, in which at least a pair of the detectors are arranged symmetrically to each other across an optical axis of the irradiation light from the light source, and in which the light quantity data is not used for the calculation of the concentration of the measurement target substance if a ratio of the light quantity data and/or difference thereof from the detectors is out of a previously-set range.

Also, an automatic analyzer according to another typical embodiment is an automatic analyzer which irradiates a reaction container arranged at a photometric position and housing mixture solution of a sample and a reagent with light from a light source, which detects scattered light or transmitted light from the mixture solution by a detector to obtain light quantity data, and which calculates a concentration of a measurement target substance in the mixture solution from the light quantity data, in which at least a pair of the detectors are arranged symmetrically to each other across an optical axis of the irradiation light from the light source in a vertical direction, and in which the reaction container housing a reference substance for calculating the concentration of the measurement target substance is arranged at the photometric position, and in which a drift amount of the light quantity data of a reference substance from each detector obtained during previously-set time is calculated prior to the calculation of the concentration of the measurement target substance.

Effects of the Invention

The effects obtained by typical aspects of the present invention will be briefly described below.

According to the present invention, at least the pair of the detectors which detect the scattered light or the transmitted light from the reaction container are arranged symmetrically to each other across the optical axis of the irradiation light from the light source, and therefore, the drift of the light quantity data caused by the thermal deformation of the optical system can be corrected by comparing values of the light quantity data of the respective detectors with each other. Therefore, an automatic analyzer can be provided, in which the draft of the light quantity data caused by the thermal deformation of the optical system caused by the variation in the temperature inside the device is corrected without the increase in the size and the complication so as to enhance accuracy and stability of data and so as to detect the measurement target substance at high sensitivity.

BRIEF DESCRIPTIONS OF THE DRAWINGS

BEST MODE FOR CARRYING OUT THE INVENTION

Hereinafter, an embodiment of the present invention will be described in detail based on the drawings. Note that components having the same function are denoted by the same reference symbols throughout all drawings for describing the embodiment, and the repetitive description thereof will be omitted as much as possible.

Figure 1:
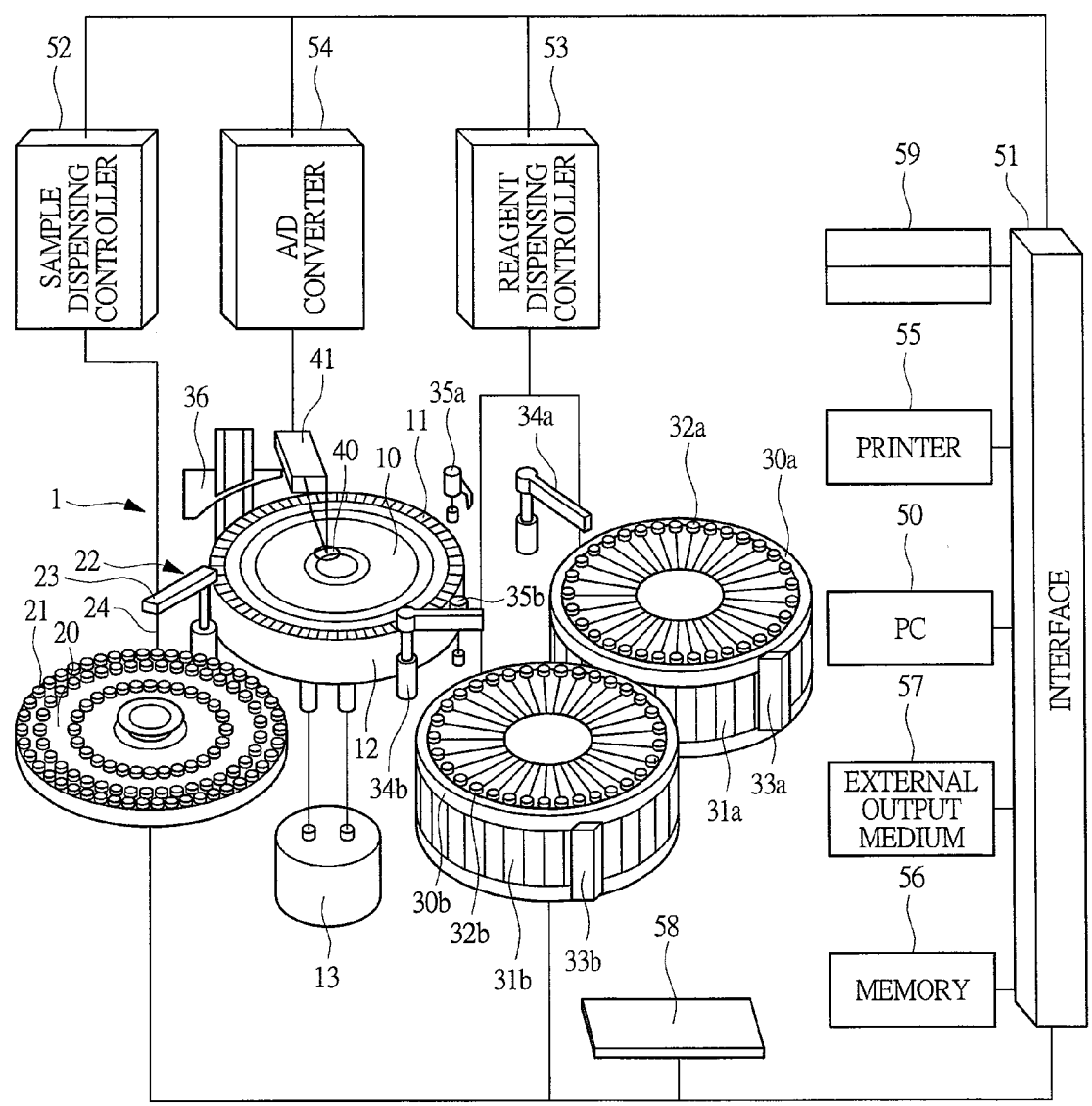
FIG. 1 is a system block diagram illustrating an overall configuration of an automatic analyzer according to an embodiment of the present invention.

FIG. 1 is a system block diagram illustrating an overall configuration of an automatic analyzer according to the embodiment of the present invention. As illustrated in FIG. 1, an automatic analyzer 1 is mainly configured of: a reaction disk 10; a sample disk 20; reagent disks 30a and 30b; a light source 40; a scattering photometer 41; and a computer 50.

The reaction disk 10 can intermittently rotate, and many reaction containers 11 made of a translucent material are mounted on the disk along a circumferential direction thereof. The reaction containers 11 are maintained at a predetermined temperature (for example, at 37° C.) by a constant-temperature bath 12. A temperature of a fluid inside the constant-temperature bath 12 is adjusted by a constant-temperature maintaining device 13.

On the sample disk 20, many specimen containers 21 for housing biological samples such as blood and urine are placed doubly along the circumferential direction in an example of the illustration. A sample dispensing mechanism 22 is arranged in vicinity of the sample disk 20. This sample dispensing mechanism 22 is mainly configured of: a movable arm 23; and a pipette nozzle 24 attached thereto. By this configuration, in the sample dispensing mechanism 22, the pipette nozzle 24 is appropriately moved to a dispensing position by the movable arm 23 upon sample dispensing, sucks a predetermined amount of the sample from the specimen container 21 positioned at a suction position of the sample disk 20, and discharges the sample into the reaction container 11 at a discharge position on the reaction disk 10.

The reagent disks 30a and 30b are disks which have the diameters and the shapes which are almost the same as each other, and have reagent refrigerators 31a and 31b arranged along the circumferential directions, respectively. In these reagent refrigerators 31a and 31b, a plurality of reagent bottles 32a and 32b on each of which a label showing reagent identification information such as a barcode is pasted are placed along the circumferential directions of the reagent disks 30a and 30b, respectively. These reagent bottles 32a and 32b house reagent solutions corresponding to analysis item which can be analyzed by the automatic analyzer 1. The barcode reading devices 33a and 33b are attached to the respective reagent refrigerators 31a and 31b, and these devices read the barcodes shown on outer walls of the respective reagent bottles 32a and 32b upon reagent registration.

The read reagent information is registered together with the positions thereof on the reagent disks 30a and 30b into a memory 56.

Also, in the vicinities of the reagent disks 30a and 30b, reagent dispensing mechanisms 34a and 34b which have mechanisms almost similar to that of the sample dispensing mechanism 22 are arranged, respectively. Upon the reagent dispensing, by pipette nozzles provided in them, the reagent solution is sucked from the reagent bottles 32a and 32b corresponding to the test items positioned at reagent receiving positions on the reaction disk 10, and is discharged into the corresponding reaction container 11.

Agitating mechanisms 35a and 35b are arranged at positions surrounded by the reaction disk 10, the reagent disks 30a and 30b, and the reagent dispensing mechanisms 34a and 34b. The mixture solution of the sample and the reagent housed inside the reaction container 11 is agitated by the agitating mechanisms 35a or 35b so as to accelerate a reaction.

The light source 40 is arranged in vicinity of the center of the reaction disk 10, the scattering photometer 41 is arranged on an outer circumferential side of the reaction disk 10, and a line of the reaction containers 11 for which the agitation is finished is moved while being rotated so as to pass through a photometric position sandwiched between the light source 40 and the scattering photometer 41. The scattering photometer 41 may be provided with a multi-wavelength absorptiometer on a position coaxially with the optical axis or a different position of the constant-temperature bath 12 so that the concentration is calculated by using both of the scattered light and the transmitted light. Note that the light source 40 and the scattering photometer 41 configure an optical detection system.

The photometry of the reaction solution of the sample and the reagent inside each reaction container 11 is measured every time the container passes across the front of the scattering photometer 41 during the rotary movement of the reaction disk 10. An analog signal of the scattered light measured for each sample is inputted to an A/D (analog/digital) converter 54. The inside of the used reaction container 11 is cleaned by a reaction-container cleaning mechanism 36 arranged in the vicinity of the reaction disk 10, so that the container can be repeatedly used.

Next, a control system and a signal processing system in the automatic analyzer 1 of FIG. 1 will be briefly explained. The computer 50 is connected to a sample-dispensing controller 52, a reagent-dispensing controller 53, and the A/D converter 54 via an interface 51. The computer 50 sends a command to the sample-dispensing controller 52 so as to control the dispensing operation for the sample. The computer 50 sends a command to the reagent-dispensing controller 53 so as to control the dispensing operation for the reagent.

A photometric value which has been converted into a digital signal by the A/D converter 54 is taken into the computer 50.

A printer 55 for printing, a memory 56 and an external output medium 57 serving as storage devices, a keyboard 58 for inputting an operation command and others, and a CRT display (display device) 59 for screen display are connected to the interface 51. As the display device 59, a liquid crystal display or others can be employed instead of the CRT display. The memory 56 is configured of, for example, a hard disk memory or an external memory. The memory 56 stores information such as a password of each operator, a display level of each screen, an analysis parameter, an analysis-item request content, a calibration result, and an analysis result.

Next, an analysis operation for the sample in the automatic analyzer 1 of FIG. 1 will be explained. The analysis parameter about the item which can be analyzed by the automatic analyzer 1 is previously inputted via an information inputting device such as the keyboard 58, and is stored in the memory 56. The operator selects a test item requested for each sample by using an operational function screen.

At this time, information such as a patient ID is also inputted from the keyboard 58. In order to analyze the test item instructed for each sample, the pipette nozzle 24 of the sample dispensing mechanism 22 dispenses a predetermined amount of the sample from the specimen container 21 to the reaction container 11 in accordance with the analysis parameter.

The reaction container 11 into which the sample has been dispensed is transported by the rotation of the reaction disk 10, and stops at the reagent receiving position. The pipette nozzles of the reagent dispensing mechanisms 34a and 34b dispense a predetermined amount of the reagent solution to the reaction container 11 in accordance with the analysis parameter of the corresponding test item. An order of dispensing the sample and the reagent may be opposite to this example so that the reagent is dispensed earlier than the sample.

Then, the sample and the reagent are agitated and mixed by the agitating mechanisms 35a and 35b. When the reaction container 11 passes across the photometric position, the photometry of the scattered light of the reaction solution is measured by the scattering photometer 41. The photometric-measured scattered light is converted into a numerical value which is proportional to the light quantity by the A/D converter 54, and the numerical value is taken into the computer 50 via the interface 51.

By using this converted numerical value, the concentration data is calculated based on a calibration curve previously measured by an analysis method specified for each test item. The component concentration data as the analysis result of each test item is outputted to the printer 55 and/or a screen of the CRT display 59.

Before the above-described measurement operation is executed, the operator sets various parameters, and registers the sample, which are required for the analysis measurement, via the operation screen of the CRT display 59. Moreover, the operator checks the analysis result obtained after the measurement by using the operational screen on the CRT display 59.

Figure 2:
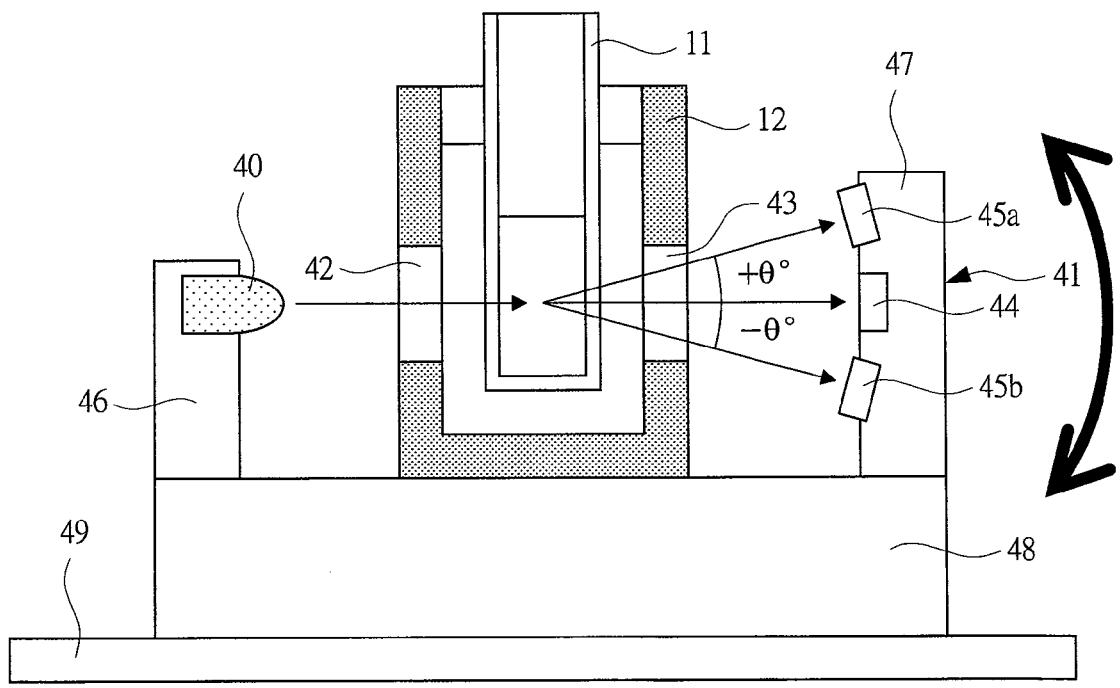
FIG. 2 is a schematic diagram of an optical system according to the embodiment of the present invention.
Figure 3:
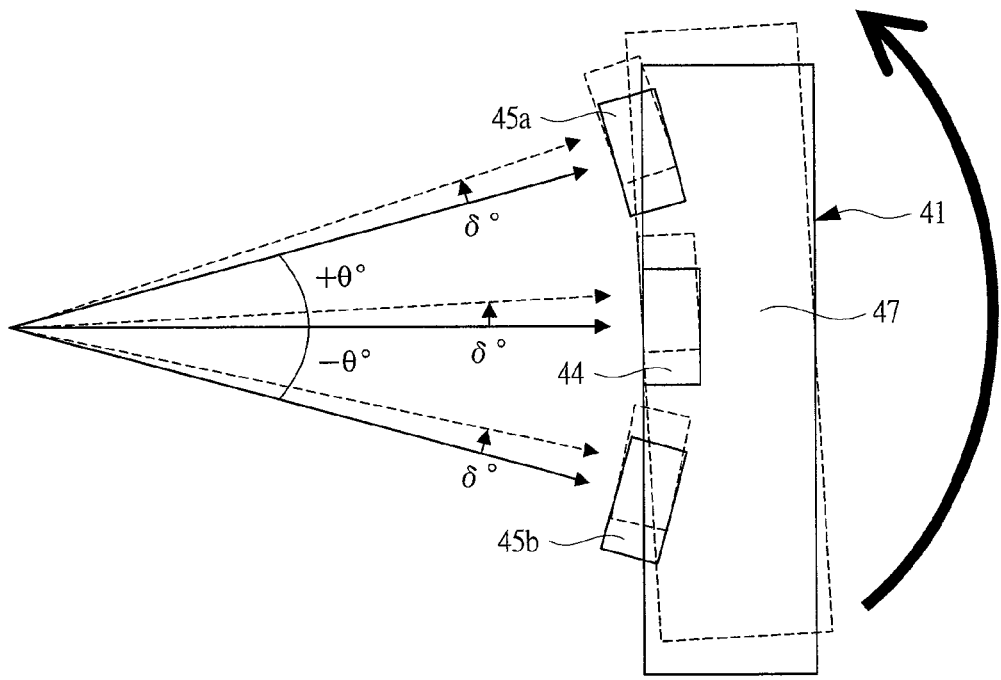
FIG. 3 is a diagram for explaining change in a light acceptance angle caused by thermal deformation of the optical system.

FIG. 2 is a schematic diagram of an optical system according to an embodiment of the present invention. The irradiation light from the light source 40 passes through a light projector window 42 so as to irradiate the measurement target substance inside the reaction container 11. The transmitted light from the measurement target substance passes through a light receiving window 43, and is received by a transmitted-light detector 44. The scattered light from the measurement target substance passes through the light receiving window 43, and is received by a pair of a detector 45a for +θ scattered light and a detector 45b for −θ scattered light which are arranged in the vertical direction symmetrically to each other across the optical axis. The light source 40 is fixed by a light-source holder (that is a base member in which the light source is arranged) 46, and the detectors 44, 45a, and 45b are arranged and fixed at equal intervals on a detector holder (that is a base member in which each detector is arranged) 47. The light-source holder 46 and the detector holder 47 are fixed to a photometer base 48, and the photometer base 48 is fixed to a mechanism base 49. While the temperature distribution inside the device is changed by operations of a motor, a circuit, a heat exchanger, and others, the temperature change immediately after the startup of the device is particularly large, and deformation as illustrated by an arrow is caused by a temperature difference between top and bottom of the device. In the turntable-type photometer, the deformation as illustrated by the arrow tends to be caused because the photometer has a shape which is opened upward so that the reaction container 11 can pass therethrough. As a portion to be deformed, due to a dimensional difference, the photometer base 48 and the mechanism base 49 have large deformation amounts while the light-source holder 46 and the detector holder 47 have small deformation amounts. Therefore, as illustrated in FIG. 3, the deformation is caused so as to be shifted by δ° while maintaining a relation of a relative position of the light acceptance angle.

Figure 4:
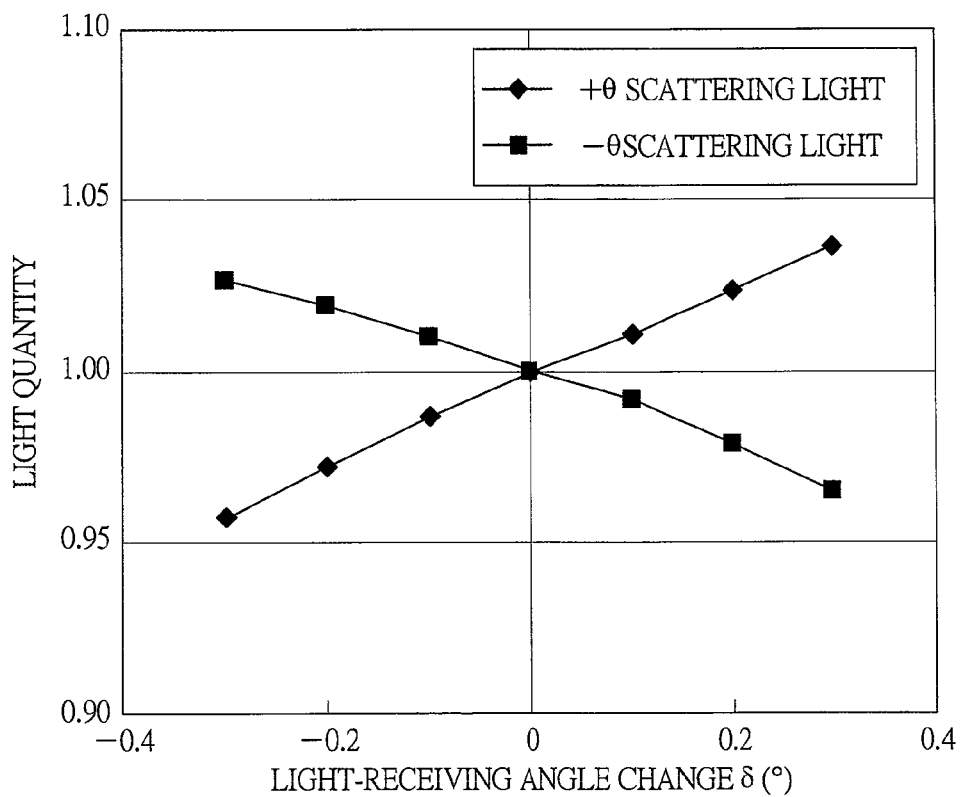
FIG. 4 is a graph illustrating measurement results of change in light quantity of ±θ scattered light caused by the change in the light acceptance angle.

FIG. 4 is a graph illustrating measurement results of the change in the light quantity of ±θ scattered light caused by the change in the light acceptance angle. That is, the results are actually-measured results of the variations in the light quantity data when an angle of the detector holder 47 is changed while maintaining a relation of a relative position of a certain light acceptance angle θ. The ±θ scattered light is theoretically supposed to have the same value, and their values almost match with each other also in the present results when there is no shift in the light acceptance angle. A proportional relation is established between the shift in the light acceptance angle and the light quantity data, and it can be understood that the sum of the ±θ light quantity data is constant. That is, it has been found out that the drift of the light quantity data derived from the thermal deformation can be corrected by taking the sum of the ±θ light quantity data, the average thereof, or both of them.

It is considered that the drift of the light quantity data is roughly categorized into (1) drift of the light source, (2) drift of an electric circuit system, and (3) drift caused by the thermal deformation of the optical system. Among them, (1) the drift of the light source and (2) the drift of the electric circuit system can be easily suppressed to a certain level by a temperature adjusting action of the light source and the electric circuit. However, (3) the drift caused by the thermal deformation of the optical system is affected by not only the deformation of the photometer but also deformation of the base on which the photometer is mounted. Further, this is also affected by complex temperature change caused between the outside air temperature and the heat sources whose operations are individually controlled to each other such as the motor, the substrate, and the heat exchanger. Therefore, it is very difficult to control them, and the significance of the correction is large.

Figure 5A:
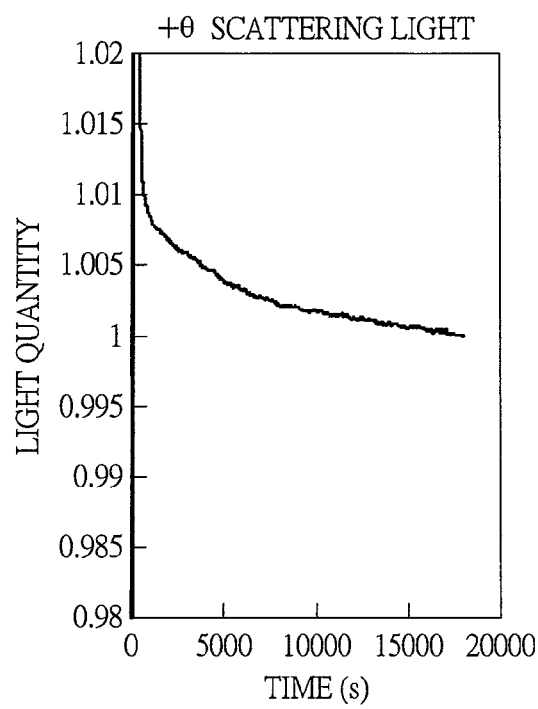
FIGS. 5A and 5B are graphs illustrating independent measurement results of ±θ scattered light after startup of the automatic analyzer, respectively.
Figure 5B:
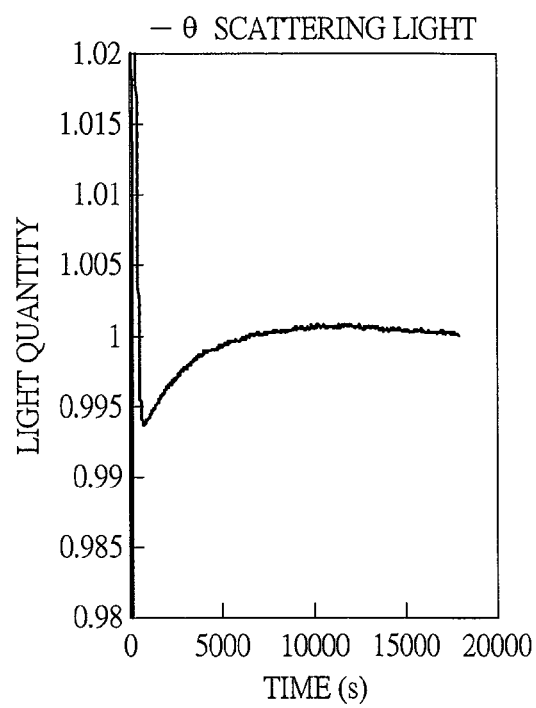
Figure 6:
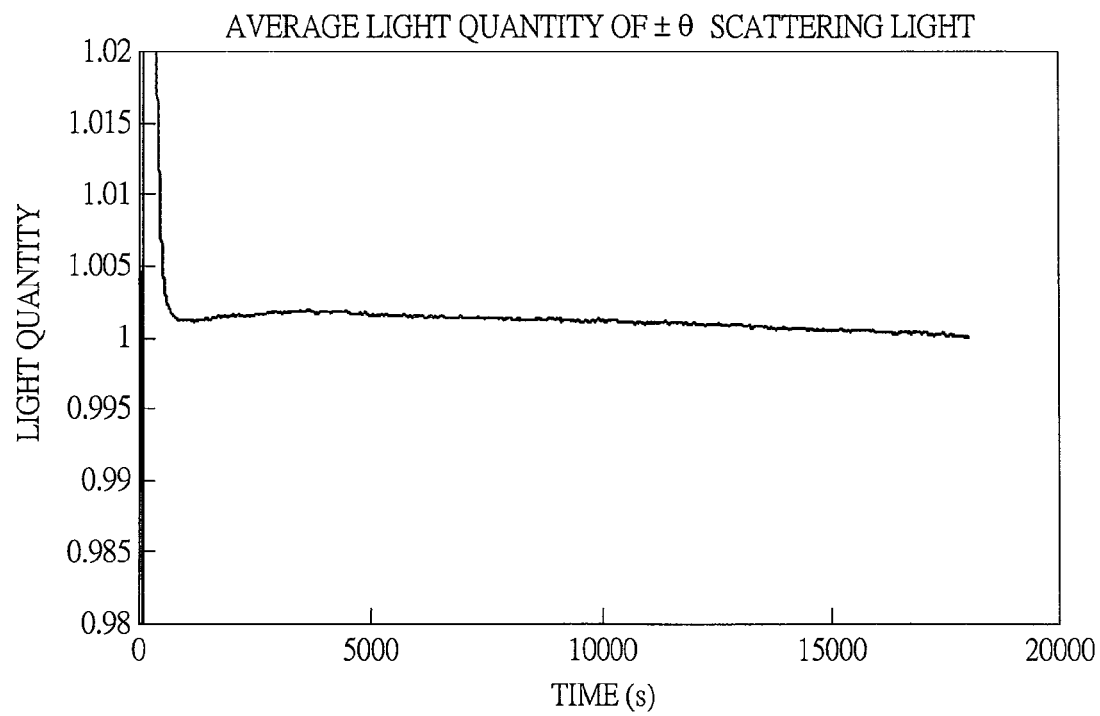
FIG. 6 is a graph illustrating an average value of the ±θ scattered light after the startup of the automatic analyzer.

FIGS. 5A and 5B are graphs illustrating independent measurement results of the ±θ scattered light after the startup of the automatic analyzer, respectively. That is, they are results obtained by measuring scattering bodies inside the reaction container for five hours after the startup of the device. Immediately after the startup of the device, both of the ±θ light quantity data are largely reduced, and this reduction is due to the drift of the LED light source having characteristics in which the light quantity is reduced when the temperature increases. When the drift of the light source are almost eliminated, the ±θ light quantity data show opposite behavior, and this is conceived to be the drift of the light quantity data caused by the thermal deformation. Accordingly, as illustrated in FIG. 6, by averaging the ±θ light quantity data, the drift caused by the thermal deformation can be corrected upon the analysis, that is, upon the calculation of the concentration of the measurement target substance. Note that FIG. 6 exemplifies the average of the ±θ light quantity data. However, the drift may be corrected based on the sum thereof, or the drift may be corrected by using both of the average and the sum thereof. In the view of FIG. 6, the average of the ±θ light quantity data is also slightly varied. However, this variation is due to the drift of the light source and the electric circuit system.

Figure 7:
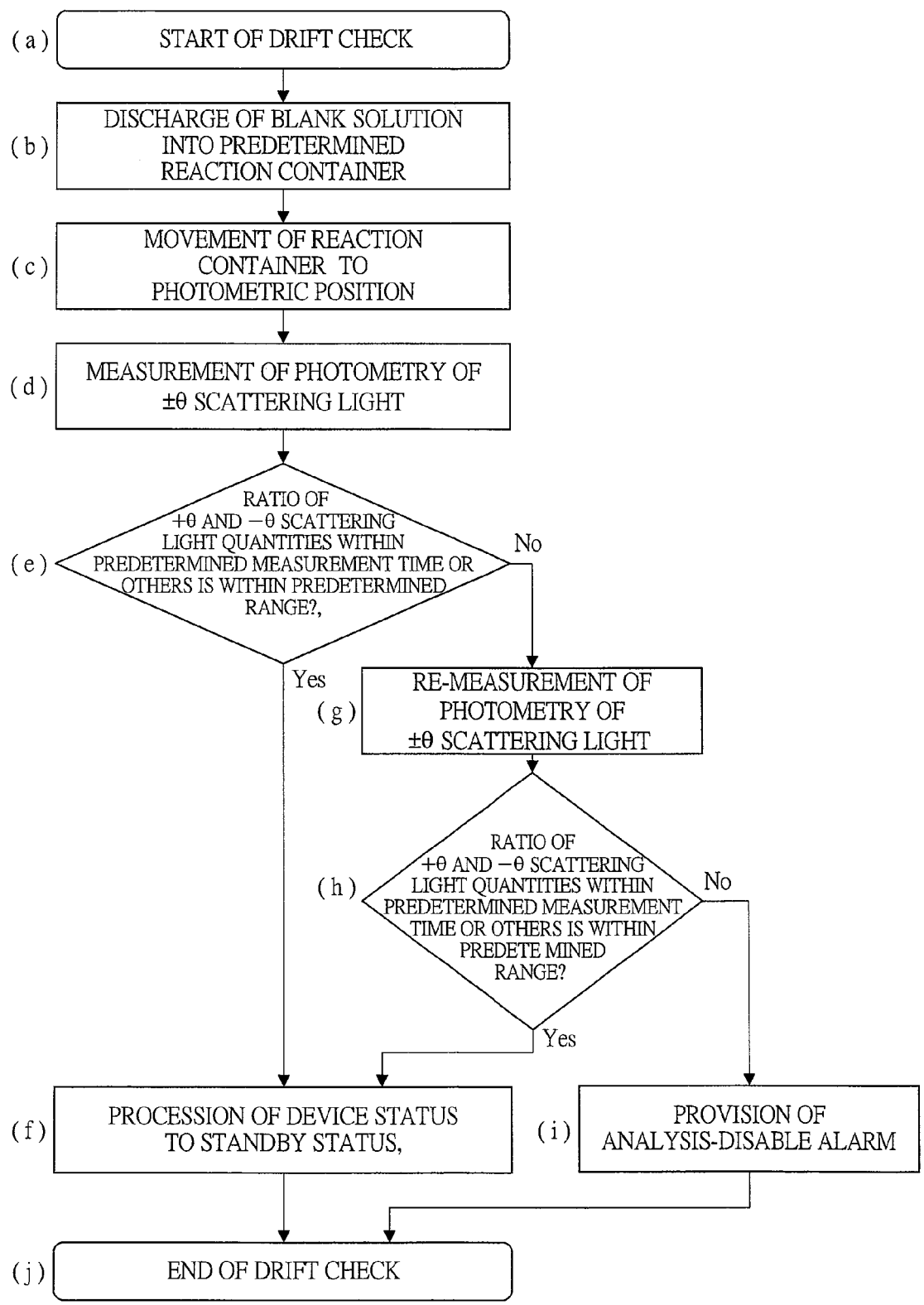
FIG. 7 is an operation flow chart including steps (a) to (j) for checking the light quantity data drift before analysis start by the automatic analyzer of the present invention.

FIG. 7 is an operation flow chart including steps (a) to (j) for checking the drift of the light quantity data before the startup of the analysis by the automatic analyzer of the present invention. This function is automatically executed before the analysis such as upon an initializing operation after the startup of the device or upon change of water in the constant-temperature bath (upon which the constant-temperature maintaining device 13 is temporarily stopped). First, when (a) the drift check is started, (b) a reference substance such as blank water or a blank solution for calculating the concentration of the measurement target substance is dispensed into a predetermined reaction container, and then, (c) the reaction container is moved to the photometric position. After the reaction container is moved, (d) measurement of the scattered light and the transmitted light is executed in a state in which the reaction container is stopped. In predetermined measurement time (such as five minutes), (e) the computer 50 checks (calculates) whether the drift caused by the thermal deformation of the optical system and the drifts of the light source and the electric circuit system are within a predetermined range or not. If these values are within the predetermined range, (f) a state of the device proceeds to a standby state. If they are out of the predetermined range, (g) the re-measurement is executed. At this time, the drift caused by the thermal deformation of the light source can be calculated by the ratio of the ±θ scattered light quantity or the difference between the ±θ scattered light quantity, and the drifts of the light source and the electric circuit system can be calculated by the average or the sum of the ±θ scattered light quantity. And, (h) the computer 50 checks whether they are within the predetermined range or not. If the ratio of the ±θ scattered light quantity, the difference between the ±θ scattered light quantity, and the drift amount of the single transmitted light or scattered light are out of the predetermined range even if the re-measurement is executed, (i) an analysis-disable alarm is sounded so that the flow does not proceed to the analysis operation (the calculation of the concentration of the measurement target substance). Then, (j) the drift check is terminated. The number of times of re-measurement can be arbitrarily set. An aim of this function is to perform the drift check of the optical system before the start of the analysis so as to determine whether the measurement is possible or not. In a conventional automatic analyzer, the management is made such that the analysis is started after a certain period of time such as 30 minutes after the startup of the device or after the change of the water in the constant-temperature bath elapses. While this certain period of time is the time required when the drift of the optical system is within an allowable range and is the experimentally-proven time, it is not actually checked whether the drifts have been converged or not. However, highly-reliable and highly-sensitivity detection can be achieved by performing the drift check before the analysis.

Figure 8:
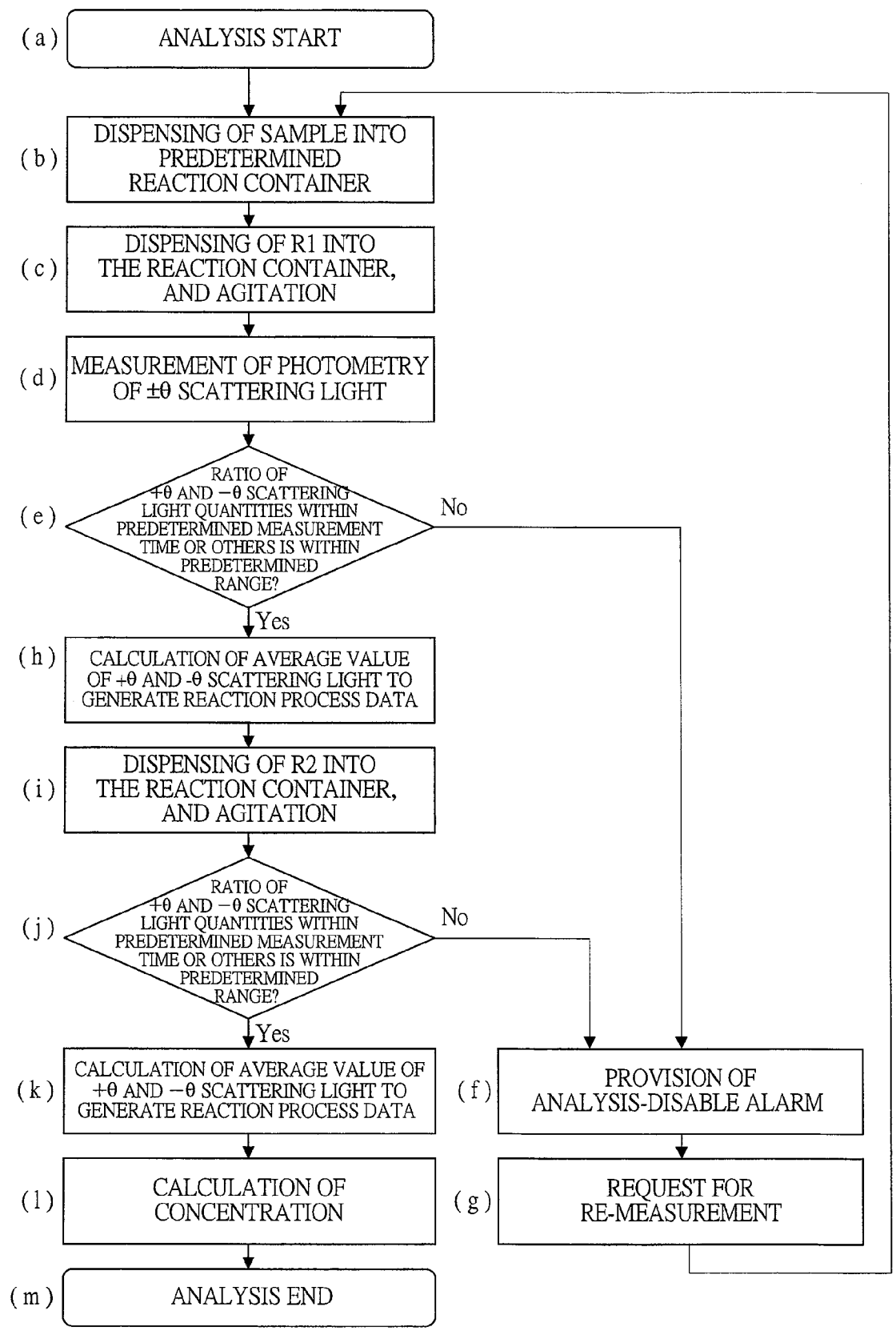
FIG. 8 is an operation flow chart including steps (a) to (m) for checking the light quantity data drift during the analysis by the automatic analyzer of the present invention.

FIG. 8 is an operation flow chart including steps (a) to (m) for checking the drift of the light quantity data during the analysis by the automatic analyzer of the present invention. Analysis items include: a one-reagent system; a two-reagent system; a three-reagent system; and others, and the present example is described by exemplifying the item of the two-reagent system (in which a first reagent and a second reagent are used). Also, generally, in the latex agglutination method, since the first reagent is a pretreatment reagent, the change in the light quantity or others is not caused even if it is mixed with the sample. However, since the second reagent contains antibody-sensitized latex particles, agglutination of the latex particles due to the antigen-antibody reaction is caused if the sample contains an antigen to be a target, which results in the change in the light quantity. This change in the light quantity is detected, so that the concentration of the target substance is quantified. The present example is described under the above-described conditions. When (a) the analysis is started, (b) the sample is dispensed into a predetermined reaction container first. Then, (c) the first reagent (R1) is dispensed, and agitation is performed. The drift caused by the thermal deformation of the light source can be calculated by the ratio of the $\pm\theta$ scattered light quantity or the difference between the $\pm\theta$ scattered light quantity obtained from the light quantity data obtained during the rotation of the reaction disk 10, and the drifts of the light source and the electric circuit system can be calculated by the average or the sum of the $\pm\theta$ scattered light quantity. And, (e) the computer 50 checks whether their values are within the predetermined range or not. If they are out of the predetermined range, (f) an analysis-disable alarm is sounded, and (g) the re-measurement is executed. If they are within the predetermined range, (h) the average or the sum of the $\pm\theta$ scattering is calculated by the computer 50 so as to generate the data regarding the reaction process. Subsequently, (i) the second reagent (R2) is dispensed into the reaction container, and agitation is performed. Similarly, the drift caused by the thermal deformation of the light source can be calculated by the ratio of the $\pm\theta$ scattered light quantity or the difference between the $\pm\theta$ scattered light quantities obtained from the light quantity data obtained during the rotation of the reaction disk 10. And, (j) the computer 50 checks whether these values are within the predetermined range or not. If they are out of the predetermined range, (f) an analysis-disable alarm is sounded, and (g) the re-measurement is executed. If they are within the predetermined range, (k) the average or the sum is calculated by the computer 50 so as to generate the data regarding the reaction process, (l) the concentration of the measurement target substance is calculated, and (m) the result is outputted so that the analysis is terminated. In a conventional automatic analyzer, the drift check of the optical system is not performed during the analysis. However, by performing the drift check of the optical system during the analysis as described above, highly-reliable and highly-sensitive detection can be achieved, and measurement results can be ensured.

In the foregoing, the invention made by the present inventors has been concretely described based on the embodiment. However, it is needless to say that the present invention is not limited to the foregoing embodiment and various modifications and alterations can be made within the scope of the present invention.

For example, in the mode illustrated in the drawings, the paired two scattered-light detectors are symmetrically arranged in the vertical direction so as to sandwich the optical axis therebetween. However, the number of them is not limited to this, and four or more detectors, that is, two or more paired detectors may be arranged.

INDUSTRIAL APPLICABILITY

The present invention can be used for an automatic analyzer and an automatic analyzing method for analyzing an amount of a component contained in a sample such as blood or urine.

SYMBOL EXPLANATION 1 automatic analyzer
10 reaction disk
11 reaction container
12 constant-temperature bath
13 constant-temperature maintaining device
20 sample disk
21 specimen container
22 sample dispensing mechanism
23 movable arm
24 pipette nozzle
30a reagent disk
30b reagent disk
31a reagent refrigerator
31b reagent refrigerator
32a reagent bottle
32b reagent bottle
33a barcode reading device
33b barcode reading device
34a reagent dispensing mechanism
34b reagent dispensing mechanism
35a agitating mechanism
35b agitating mechanism
36 reaction-container cleaning mechanism
40 light source
41 scattering photometer
42 light projector window
43 light receiving window
44 transmitted-light detector
45a detector for $+\theta$ scattered light
45b detector for $-\theta$ scattered light
46 light-source holder (that is a base member in which the light source is arranged)
47 detector holder (that is a base member in which each detector is arranged)
48 photometer base
49 mechanism base
50 computer
51 interface
52 sample-dispensing controller
53 reagent-dispensing controller
54 A/D converter
55 printer
56 memory
57 external output medium
58 keyboard
59 CRT display (display device)

The invention claimed is:
1. An automatic analyzer comprising:
a reaction disk that retains a plurality of reaction containers disposed circumferentially around the reaction disk and that repeatedly rotates and stops;
a light source disposed on a first base member that irradiates a reaction container with light, the reaction container being arranged at a photometric position and housing a mixture solution of a reagent and a sample retained in reaction container on the reaction disk;
a first detector disposed on a second base member that detects transmitted light from the mixture solution;
one or more pairs of second detectors, that detect scattered light from the mixture solution, disposed on the second base member in a plane perpendicular to a direction of movement of the reaction disk, and the second detectors of each of the one or more pairs of second detectors are disposed symmetrically with respect to the first detector in the plane perpendicular to a direction of movement of the reaction disk and are each positioned at an angle having the same absolute value relative to the optical axis of irradiation of the light from the light source; and a controller programmed to compensate for thermal deformation of the first detector and the one or more pairs of second detectors by using one of an averaged value of light quantity data and a sum thereof from the first detector and the one or more pairs of second detectors to calculate a concentration of a measurement target substance in the mixture solution, wherein the first base member and the second base member are disposed on a third base member.

2. The automatic analyzer according to claim 1,
wherein, if a ratio of light quantity data or a difference between light quantity data obtained from the one or more pairs of second detectors is out of a previously-set range, the light quantity data is not used for the calculation of the concentration of the measurement target substance.

3. The automatic analyzer according to claim 2,
wherein, if an averaged value of light quantity data or a sum thereof from the one or more pairs of second detectors is out of a previously-set range, the light quantity data is not used for the calculation of the concentration of the measurement target substance.

4. The automatic analyzer according to claim 2,
wherein a reaction container that houses a reference substance for the calculation of the concentration of the measurement target substance is arranged at the photometric position, and a drift amount of the light quantity data of the reference substance from each of the detectors at previously-set time is calculated prior to the calculation of the concentration of the measurement target substance.

5. The automatic analyzer according to claim 4,
wherein, if the drift amount is out of a previously-set range, a process does not proceed to the calculation of the concentration of the measurement target substance.

6. The automatic analyzer according to claim 5,
wherein the drift amount is a ratio of light quantity data or difference thereof from the respective detectors.

7. The automatic analyzer according to claim 5,
wherein the drift amount is an averaged value of light quantity data or a sum thereof from the respective detectors.

* * * * *